US008426658B2

(12) United States Patent
Pham et al.

(10) Patent No.: US 8,426,658 B2
(45) Date of Patent: Apr. 23, 2013

(54) AZEOTROPE-LIKE COMPOSITION OF 2-CHLORO-1,1,1,2-TETRAFLUOROPROPANE (HCFC-244BB) AND HYDROGEN FLUORIDE (HF)

(75) Inventors: Hang T. Pham, Amherst, NY (US);
Rajiv R. Singh, Getzville, NY (US);
Hsueh Sung Tung, Getzville, NY (US);
Konstantin A. Pokrovski, Orchard Park, NY (US); Daniel C. Merkel, Orchard Park, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/284,319

(22) Filed: Oct. 28, 2011

(65) Prior Publication Data
US 2012/0037843 A1 Feb. 16, 2012

Related U.S. Application Data

(62) Division of application No. 12/368,395, filed on Feb. 10, 2009, now Pat. No. 8,070, 975.

(60) Provisional application No. 61/031,602, filed on Feb. 26, 2008.

(51) Int. Cl.
*C07C 17/38* (2006.01)
(52) U.S. Cl.
USPC .......................................... 570/178; 570/177
(58) Field of Classification Search .................. 570/177, 570/178
See application file for complete search history.

(56) References Cited

U.S. PATENT DOCUMENTS

| 6,107,267 | A | 8/2000 | Rao et al. |
| 6,500,795 | B2 | 12/2002 | Pham et al. |
| 6,534,467 | B2 | 3/2003 | Pham et al. |
| 6,903,063 | B2 * | 6/2005 | Pham et al. .................. 510/408 |
| 2005/0245421 | A1 | 11/2005 | Singh et al. |
| 2005/0247905 | A1 | 11/2005 | Singh et al. |
| 2007/0007488 | A1 | 1/2007 | Singh et al. |
| 2007/0197842 | A1 | 8/2007 | Mukhopadhyay et al. |
| 2008/0075673 | A1 | 3/2008 | Knopeck et al. |
| 2008/0308763 | A1 | 12/2008 | Singh et al. |

FOREIGN PATENT DOCUMENTS

| WO | 97/05089 A1 | 2/1997 |
| WO | 02/059067 A1 | 8/2002 |

OTHER PUBLICATIONS

Kim, et al., "A Study to Determine The Existence of an Azeotropic R-22 "Drop-In" Substitute," prepared by U.S. Department of Commerce for Electric Power Research Institute, Mar. 1996, pp. 1-45, U.S.
Morrison, et al., "Azeotropy in Refrigerant Mixtures," International Journal of Refrigeration, 1993, pp. 129-138, vol. 16, No. 2. U.S.

* cited by examiner

*Primary Examiner* — Jafar Parsa
(74) *Attorney, Agent, or Firm* — Bruce O. Bradford

(57) ABSTRACT

Provided are azeotropic and azeotrope-like compositions of 2-chloro-1,1,1,2-tetrafluoropropane (HCFC-244bb) and hydrogen fluoride (HF). Such azeotropic and azeotrope-like compositions are useful as intermediates in the production of 2,3,3,3-tetrafluoropropene (HFO-1234yf).

8 Claims, 1 Drawing Sheet

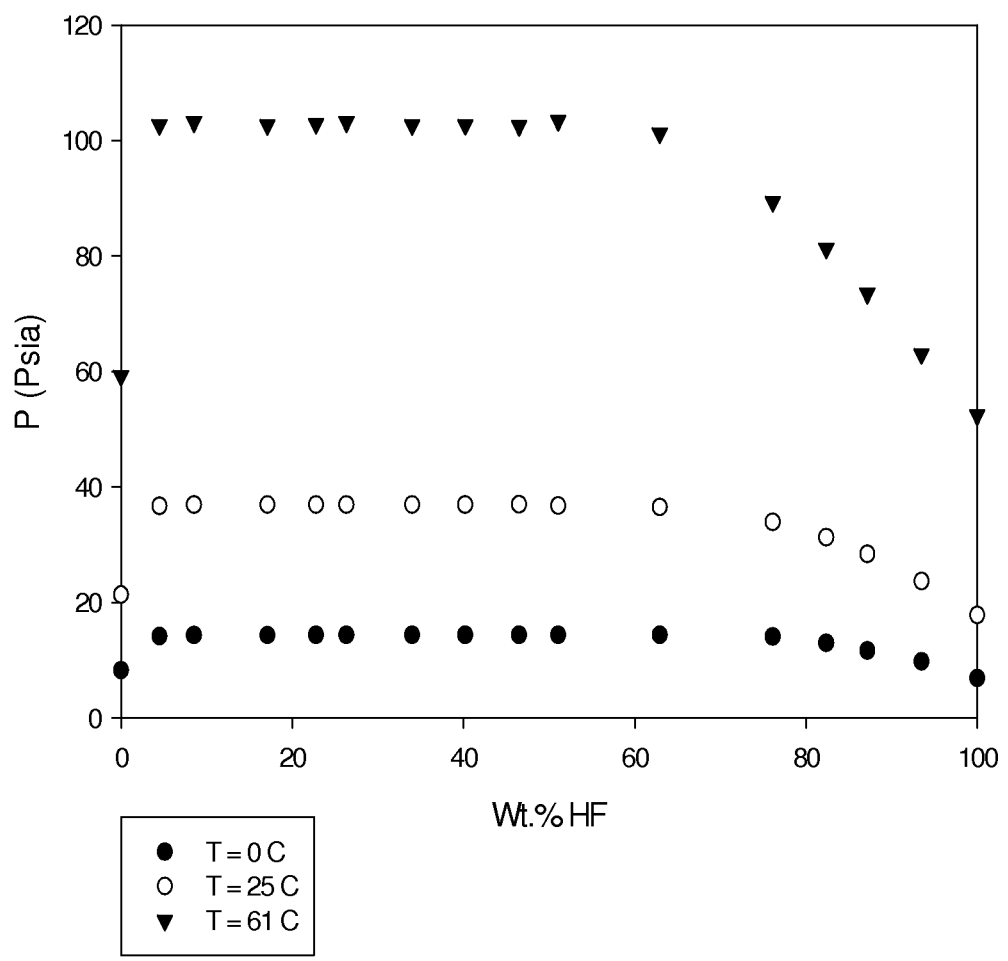

AZEOTROPE-LIKE COMPOSITION OF 2-CHLORO-1,1,1,2-TETRAFLUOROPROPANE (HCFC-244BB) AND HYDROGEN FLUORIDE (HF)

CROSS REFERENCE TO RELATED APPLICATION

This application is a Divisional of U.S. application Ser. No. 12/368,395, filed on Feb. 10, 2009 (now U.S. Pat. No. 8,070,975), which claims priority benefit of U.S. Provisional Application No. 61/031,602 filed Feb. 26, 2008, each of which are incorporated herein by reference.

BACKGROUND OF THE INVENTION

1. Field of the Invention

The present invention pertains to azeotropic and azeotrope-like compositions of 2-chloro-1,1,1,2-tetrafluoropropane (HCFC-244bb) and hydrogen fluoride (HF). More particularly the invention pertains to such azeotropic and azeotrope-like compositions which are useful as intermediates in the production of 2,3,3,3-tetrafluoropropene (HFO-1234yf).

2. Description of the Related Art

Traditionally, chlorofluorocarbons (CFCs) like trichlorofluoromethane and dichlorodifluoromethane have been used as refrigerants, blowing agents and diluents for gaseous sterilization. In recent years there has been universal concern that completely halogenated chlorofluorocarbons might be detrimental to the Earth's ozone layer. Therefore, stratospherically safer alternatives to these materials are desirable. Consequently, there is a worldwide effort to use fluorine-substituted hydrocarbons which contain fewer or no chlorine substituents. In this regard, 2-chloro-1,1,1,2-tetrafluoropropane (HCFC-244bb) having low ozone depletion potential, is being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are non-flammable, and non-toxic as compared to the chlorine containing compounds.

HCFC-244bb is an intermediate in the production of 2,3,3,3-tetrafluoropropene (HFO-1234yf) which is well known in the art as described in U.S. Applications 20070007488 and 20070197842, the specifications of which are incorporated herein by reference. HFO-1234yf has been disclosed to be an effective refrigerant, fire extinguishant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

It has now been found that an important intermediate in the production of substantially pure HFO-1234yf, is an azeotropic or azeotrope-like composition of 2-chloro-1,1,1,2-tetrafluoropropane (HCFC-244bb) and hydrogen fluoride. This intermediate, once formed, may thereafter be separated into its component parts by known extraction techniques. The azeotropic and azeotrope-like compositions find use not only as intermediates in the production of HFO-1234yf, but they are additionally useful as nonaqueous etchant mixtures for etching semiconductors in the electronics industry, as well as compositions for removing surface oxidation from metals. In addition, the formation of an azeotropic or azeotrope-like composition of HCFC-244bb and hydrogen fluoride is useful in separating a mixture of HCFC-244bb and an impurity such as a halocarbon, for example, 2,3,3,3-tetrafluoropropene, 1,2-dichloro-3,3,3-trifluoropropene, or 1,1,1,2,2-pentafluoropropane. When it is desired to separate a mixture of HCFC-244bb and an impurity, HF is added to form an azeotropic mixture of HCFC-244bb and hydrogen fluoride, and then the impurity is removed from the azeotropic mixture, such as by distillation, scrubbing or other known means.

SUMMARY OF THE INVENTION

The invention provides an azeotropic or azeotrope-like composition consisting essentially of hydrogen fluoride and 2-chloro-1,1,1,2-tetrafluoropropane.

The invention further provides an azeotropic or azeotrope-like composition which consists essentially of from about 1 to about 50 weight percent hydrogen fluoride and from about 50 to about 99 weight percent 2-chloro-1,1,1,2-tetrafluoropropane, which composition has a boiling point of from about 0° C. to about 61° C. at a pressure of from about 14 psia to about 103 psia.

The invention also provides a method of forming an azeotropic or azeotrope-like composition which comprises forming a blend consisting essentially of from about 1 to about 50 weight percent hydrogen fluoride and from about 50 to about 99 weight percent 2-chloro-1,1,1,2-tetrafluoropropane to thereby form an azeotropic or azeotrope-like composition having a boiling point of from about 0° C. to about 61° C. at a pressure of from about 14 psia to about 103 psia.

The invention still further provides a method for removing 2-chloro-1,1,1,2-tetrafluoropropane from a mixture containing 2-chloro-1,1,1,2-tetrafluoropropane and at least one impurity, which comprises adding hydrogen fluoride to the mixture in an amount sufficient to form an azeotropic or azeotrope-like composition of the 2-chloro-1,1,1,2-tetrafluoropropane and the hydrogen fluoride, and thereafter separating the azeotropic composition from the impurity.

BRIEF DESCRIPTION OF THE DRAWING

FIG. 1 shows a plot of the vapor pressures of the mixtures formed in Example 2 as measured at 0° C., 25° C. and 61° C.

DETAILED DESCRIPTION OF THE INVENTION

In a method of preparing a HCFC-244bb precursor, reagents are fluorinated with hydrogen fluoride. This may be done, for example, by the liquid phase or gas phase catalytic fluorination of $CF_3CCl=CH_2$ (HCFO-1233xf) with HF to yield HCFC-244bb. Such methods are disclosed in U.S. Applications 20070007488 and 20070197842. The reaction products of such precursors include HCFC-244bb, unreacted HF and other by-products. Upon removal of the by-products, a binary azeotrope or azeotrope-like composition of HCFC-244bb and HF is formed. This binary azeotrope or azeotrope-like composition is then available for separation into its component parts. The azeotropic or azeotrope-like compositions of the HCFC-244bb and HF are also useful as recycle to the fluorination reactor. Thus, for example, in a process for producing HCFC-244bb, one can recover a portion of the HCFC- 244bb as an azeotropic or azeotrope-like composition of HCFC-244bb and HF and then recycle the composition to the reactor.

HCFC-244bb forms azeotropic and azeotrope-like mixtures with HF. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of hydrogen fluoride and HCFC-244bb to form an azeotropic or azeotrope-like composition. By effective amount is meant an amount of each component which, when combined with the other component, results in the formation of an azeotrope or azeotrope-like mixture. The inventive compositions preferably are binary azeotropes which consist essentially of combinations of only hydrogen fluoride with HCFC-244bb.

In the preferred embodiment, the inventive composition contains from about 1 to about 50 weight percent HF, preferably from about 15 weight percent to about 40 weight percent and most preferably from about 22 weight percent to about 33 weight percent based on the weight of the azeotropic or azeotrope-like composition.

In a preferred embodiment, the inventive composition contains from about 50 to about 99 weight percent HCFC-244bb, preferably from about 60 weight percent to about 85 weight percent and most preferably from about 67 weight percent to about 78 weight percent based on the weight of the azeotropic or azeotrope-like composition.

The composition of the present invention preferably has a boiling point of about from 0° C. to about 61° C. at a pressure of about 14 psia to about 103 psia. In one embodiment it has a boiling point of about 0° C. at a pressure of about 14 psia. In another embodiment it has a boiling point of about 25° C. at a pressure of about 37 psia. In another embodiment it has a boiling point of about 61° C. at a pressure of about 103 psia. An azeotropic or azeotrope-like composition having about 27±2 weight percent HF and about 73±2 weight percent HCFC-244bb was found at 23° C.

In another embodiment of the invention, 2-chloro-1,1,1,2-tetrafluoropropane (HCFC-244bb) may be removed from a mixture containing 2-chloro-1,1,1,2-tetrafluoropropane (HCFC-244bb) and an impurity which may, for example, result from manufacturing steps in the preparation of 2-chloro-1,1,1,2-tetrafluoropropane (HCFC-244bb). This is done by adding hydrogen fluoride to the mixture of the 2-chloro-1,1,1,2-tetrafluoropropane (HCFC-244bb) and impurity. Hydrogen fluoride is added to the mixture in an amount sufficient to form an azeotropic composition of the 2-chloro-1,1,1,2-tetrafluoropropane (HCFC-244bb) and the hydrogen fluoride, and thereafter the azeotropic composition is separated from the impurity, for example by distillation, scrubbing, or other art recognized separating means. In one embodiment, the impurity itself does not form an azeotropic mixture with 2-chloro-1,1,1,2-tetrafluoropropane (HCFC-244bb), hydrogen fluoride or a mixture of 2-chloro-1,1,1,2-tetrafluoropropane (HCFC-244bb) and hydrogen fluoride. In another embodiment, the impurity does form an azeotropic mixture with 2-chloro-1,1,1,2-tetrafluoropropane (HCFC-244bb), hydrogen fluoride or a mixture of 2-chloro-1,1,1,2-tetrafluoropropane (HCFC-244bb) and hydrogen fluoride. Typical impurities for 2-chloro-1,1,1,2-tetrafluoropropane (HCFC-244bb) include other halocarbons which may be miscible with 2-chloro-1,1,1,2-tetrafluoropropane (HCFC-244bb) such as 2,3,3,3-tetrafluoropropene; 1,1,1,2-pentafluoropropane or 1,2-dichloro-3,3,3-trifluoropropene.

The following non-limiting examples serve to illustrate the invention.

EXAMPLE 1

73 g of 2-chloro-1,1,1,2-tetrafluoropropane (HCFC-244bb) were mixed with 27 g of HF to form a heterogeneous azeotrope mixture. The vapor pressure of the mixture at about 25° C. was about 37 psia.

EXAMPLE 2

Binary compositions containing solely 2-chloro-1,1,1,2-tetrafluoropropane (HCFC-244bb) and HF were blended to form a heterogeneous azeotrope mixtures at different compositions. The vapor pressures of the mixtures were measured at about 0° C., 25° C. and 61° C. and the following results were noticed. Table 1 shows a P-T-X phase equilibrium and vapor pressure measurements of HCFC-244bb and HF as a function of composition with varying weight percent HF at constant temperatures of about 0° C., 25° C., and 61° C. The data also showed that HCFC-244bb/HF is a heterogeneous mixture.

TABLE 1

P-T-X of HCFC-244bb/HF System

| | Pressure (Psia) | | |
|---|---|---|---|
| Wt. % HF | T = 0° C. | T = 25° C. | T = 61° C. |
| 0.00 | 8.24 | 21.33 | 59.25 |
| 4.50 | 14.16 | 36.70 | 102.69 |
| 8.52 | 14.3 | 36.90 | 103.17 |
| 17.10 | 14.3 | 36.94 | 102.69 |
| 22.78 | 14.35 | 36.94 | 102.88 |
| 26.33 | 14.35 | 36.94 | 103.17 |
| 34.01 | 14.35 | 36.94 | 102.69 |
| 40.20 | 14.35 | 36.94 | 102.73 |
| 46.49 | 14.35 | 36.99 | 102.54 |
| 51.06 | 14.35 | 36.75 | 103.41 |
| 62.92 | 14.35 | 36.51 | 101.28 |
| 76.13 | 14.06 | 33.94 | 89.40 |
| 82.36 | 12.99 | 31.27 | 81.26 |
| 87.17 | 11.68 | 28.41 | 73.50 |
| 93.50 | 9.79 | 23.66 | 63.03 |
| 100.00 | 6.87 | 17.82 | 52.43 |

The data also shows that the mixture is azeotropic or azeotrope-like since the vapor pressure of the mixtures of HCFC-244bb and HF is higher, at all indicated blend proportions, than vapor pressures of HCFC-244bb and HF alone, i.e. as indicated in the first and last rows of Table 1 when HF is 0.0 wt. % and 244bb is at 100.0 wt. % as well as when 244bb is at 0.0 wt. % and HF is at 100.0 wt. %.

The data from Table 1 is shown in graphic form in FIG. 1.

EXAMPLE 3

The azeotropic or azeotrope-like composition of the HCFC-244bb/HF mixture was also verified by Vapor-Liquid-Liquid equilibrium (VLLE) experiment.

60 g of 2-chloro-1,1,1,2-tetrafluoropropane (HCFC-244bb) were mixed with 30 g of HF to form a heterogeneous mixture (visual observation) at 23° C. The vapor composition, upper liquid (HF rich), and bottom liquid (organic) were sampled. The result shows that the azeotropic composition is about 27±2 wt % HF at 23° C.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A method for removing 2-chloro-1,1,1,2-tetrafluoropropane from a mixture containing 2-chloro-1,1,1,2-tetrafluoropropane and at least one impurity, which comprises adding hydrogen fluoride to the mixture in an amount sufficient to form an azeotropic or azeotrope-like composition of the 2-chloro-1,1,1,2-tetrafluoropropane and the hydrogen fluoride, and thereafter separating the azeotropic composition from the impurity.

2. The method of claim 1 wherein the impurity does not form an azeotropic mixture with 2-chloro-1,1,1,2-tetrafluoropropane, hydrogen fluoride or a mixture of 2-chloro-1,1,1,2-tetrafluoropropane and hydrogen fluoride.

3. The method of claim 1 wherein the impurity does form an azeotropic mixture with 2-chloro-1,1,1,2-tetrafluoropropane, hydrogen fluoride or a mixture of 2-chloro-1,1,1,2-tetrafluoropropane and hydrogen fluoride.

4. The method of claim 1 wherein the impurity comprises a halocarbon.

5. The method of claim 1 wherein the impurity is miscible with 2-chloro-1,1,1,2-tetrafluoropropane.

6. The method of claim 1 wherein the impurity comprises one or more of 2,3,3,3-tetrafluoropropene; 1,1,1,2,2-pentafluoropropane; and 1,2-dichloro-3,3,3-trifluoropropene.

7. The method of claim 1 wherein the separating is conducted by distillation.

8. The method of claim 1 wherein the azeotropic composition consists essentially of from about 1 to about 50 weight percent hydrogen fluoride and from about 50 to about 99 weight percent 2-chloro-1,1,1,2-tetrafluoropropane.

* * * * *